(12) United States Patent
Birch

(10) Patent No.: US 8,998,962 B2
(45) Date of Patent: Apr. 7, 2015

(54) OSTEOSYNTHESIS PLATE FOR LUMBOSACRAL JOINT

(75) Inventor: Nicholas Birch, Northamptonshire (GB)

(73) Assignee: Medicrea International, Neyron (FR)

(*) Notice: Subject to any disclaimer, the term of this patent is extended or adjusted under 35 U.S.C. 154(b) by 0 days.

(21) Appl. No.: 13/979,386

(22) PCT Filed: Feb. 1, 2012

(86) PCT No.: PCT/IB2012/050464
§ 371 (c)(1),
(2), (4) Date: Jul. 12, 2013

(87) PCT Pub. No.: WO2012/104794
PCT Pub. Date: Aug. 9, 2012

(65) Prior Publication Data
US 2013/0296938 A1 Nov. 7, 2013

(30) Foreign Application Priority Data
Feb. 3, 2011 (FR) ...................... 11 50885

(51) Int. Cl.
*A61B 17/88* (2006.01)
*A61B 17/70* (2006.01)
*A61B 17/80* (2006.01)

(52) U.S. Cl.
CPC ......... *A61B 17/7055* (2013.01); *A61B 17/7059* (2013.01); *A61B 17/8047* (2013.01)

(58) Field of Classification Search
USPC .......... 606/246, 266, 280, 283, 286–291, 297
See application file for complete search history.

(56) References Cited

U.S. PATENT DOCUMENTS

| 6,793,658 B2* | 9/2004 | LeHuec et al. ............... 606/86 B |
| 2002/0147450 A1 | 10/2002 | Lehuec |
| 2003/0153912 A1* | 8/2003 | Graf ............................... 606/61 |
| 2004/0034356 A1 | 2/2004 | Lehuec |
| 2004/0039387 A1* | 2/2004 | Gause et al. .................... 606/69 |
| 2007/0233108 A1 | 10/2007 | Stalcup |
| 2007/0270965 A1* | 11/2007 | Ferguson ................... 623/17.11 |
| 2007/0288004 A1* | 12/2007 | Alvarez ......................... 606/61 |
| 2008/0300634 A1* | 12/2008 | Gray ............................ 606/280 |
| 2009/0163960 A1* | 6/2009 | Binder et al. ................. 606/280 |

(Continued)

FOREIGN PATENT DOCUMENTS

EP 1459690 9/2004

*Primary Examiner* — Jerry Cumberledge
*Assistant Examiner* — Tessa Matthews
(74) *Attorney, Agent, or Firm* — Defillo & Associates, Inc.; Evelyn A. Defillo

(57) ABSTRACT

The plate (1) has a generally triangular shape and includes two juxtaposed lower holes (7), intended to receive implantation screw (2) in the sacrum (100), and a first upper hole (8) for receiving an implantation screw (2) in the fifth lumbar vertebra (101). According to the invention, the plate (1) includes an extension (6) integral therewith, extending its upper side, i.e. protruding from the side opposite the two juxtaposed lower holes (7), the extension (6) having a second upper hole (15) formed in its entirety thereon, for receiving a second screw (2) intended to be implanted in the fifth lumbar vertebra (101), and having, at all points of its length, a width not greater than two times the diameter of the second upper hole (15); the direction in which the extension (6) protrudes from the plate (1) is such that the first upper hole (8) and the second upper hole (15) are placed on a first line (L1) substantially perpendicular to a second line (L2) passing through the two juxtaposed lower holes (7).

8 Claims, 4 Drawing Sheets

(56) References Cited

U.S. PATENT DOCUMENTS

| | | | |
|---|---|---|---|
| 2009/0192549 A1* | 7/2009 | Sanders et al. | 606/280 |
| 2010/0010541 A1* | 1/2010 | Boomer et al. | 606/246 |
| 2011/0196423 A1* | 8/2011 | Ziolo et al. | 606/246 |
| 2011/0288587 A1* | 11/2011 | Kozak et al. | 606/246 |
| 2012/0078252 A1* | 3/2012 | Huebner et al. | 606/70 |
| 2012/0159364 A1* | 6/2012 | Hyun | 715/766 |
| 2013/0304124 A1* | 11/2013 | Dube et al. | 606/246 |

* cited by examiner

OSTEOSYNTHESIS PLATE FOR LUMBOSACRAL JOINT

CROSS REFERENCE TO RELATED APPLICATION

This application is a national stage entry of PCT/IB2012/050464 filed Feb. 1, 2012, under the International Convention claiming priority over French Application No. 1150885 filed Feb. 3, 2011.

FIELD OF THE INVENTION

The present invention relates to a plate for the osteosynthesis of the lumbosacral joint.

BACKGROUND OF THE INVENTION

It is well known to perform the osteosynthesis of two vertebrae in case of an ailment of the intervertebral disk, i.e. to perform an immobilization of those two vertebrae and a bone fusion thereof via the implantation of osteosynthesis material.

A first technique consists of operating through the posterior route, and implanting, on the posterior side of the vertebrae, equipment with pedicular screws and connecting rods. This approach does, however, have the drawbacks of not allowing very easy access to the intervertebral disk and of being delicate to implement given the proximity to the spinal cord.

Another technique consists of operating through the anterior route, on the anterior side of the vertebrae, an osteosynthesis plate immobilizing the two vertebrae relative to each other using screws engaged in holes comprised by said plate.

One existing plate for performing the osteosynthesis of the lumbosacral joint through the anterior route, described by document N° US 2002/147450, is generally in the shape of an isosceles triangle, and comprises two juxtaposed lower holes, intended to receive implantation screws in the sacrum, and one upper hole intended to receive an implantation screw in the fifth lumbar vertebra. This triangular shape of the plate allows the latter to be able to be placed without mobilization, or without excessive mobilization, of the bifurcations of the vena cave and the aorta, situated just above the lumbosacral joint. It does, however, have the significant drawback of not guaranteeing complete immobilization of the fifth lumbar vertebra, which is not without impact on the osteosynthesis performed.

To resolve this drawback, it is known from document N° US 2007/233108 to use square plates, comprising two lower holes for receiving fastening screws in the sacrum and two upper holes for receiving fastening screws in the fifth lumbar vertebra. This plate allows better fastening in the fifth lumbar vertebra, but has the significant drawback of requiring a substantial and delicate immobilization of the bifurcations of the vena cave and the aorta, making the operation much more complex. Document N° US 2004/034356 also describes a square vertebral plate.

OBJECTS OF THE INVENTION

The present invention aims to resolve the aforementioned drawbacks, by providing a plate for the osteosynthesis of the lumbosacral joint that allows both complete fixing in the fifth lumbar vertebra and reduced or no mobilization of the bifurcations of the vena cave and the aorta.

SUMMARY OF THE INVENTION

The concerned plate has, in a known manner, a generally triangular shape and comprises two juxtaposed lower holes, intended to receive implantation screws in the sacrum, and a first upper hole for receiving an implantation screw in the fifth lumbar vertebra.

According to the invention, the plate comprises an extension integral therewith, extending its upper side, i.e. protruding from the side opposite the two juxtaposed lower holes, said extension having a second upper hole formed in its entirety thereon, for receiving a second screw intended to be implanted in the fifth lumbar vertebra, and having, at all points of its length, a width not greater than two times the diameter of said second upper hole; the direction in which said extension protrudes from the plate is such that said first upper hole and said second upper hole are placed on a first line substantially perpendicular to a second line passing through the two juxtaposed lower holes.

Due to its triangular shape, the plate according to the invention is adapted to be placed in the lower part of the space defined by the lower branches of the bifurcations of the vena cave (iliac veins) and the aorta (iliac arteries), opposite the first vertebra of the sacrum; the upper extension is adapted to be placed in the upper part of that same space, opposite the fifth lumbar vertebra.

Owing to said upper hole, this extension can receive an implantation screw in the fifth lumbar vertebra, in addition to the screw received in said first upper hole; these two screws ensure complete immobilization of said vertebra relative to the sacrum. The width of said extension is, however, reduced over the entire length thereof, which makes it possible to limit the mobilization to be done on the bifurcations of the vena cave and the aorta, or even to eliminate that mobilization.

It will be understood that the term "length" designates the dimension of the extension in a direction parallel to said first line and "width" designates the dimension of said extension in a direction perpendicular to said length, therefore parallel to said second line.

It will also be understood that the expression "protruding" means that said extension projects past the generally triangular contour of the plate.

Furthermore, the expression "placed on a first line" must be understood as including the fact that the center of said first upper hole and the center of said second upper hole may or may not be situated on said first line. Likewise, the expression "placed on a second line" must be understood as including the fact that the center of the lower holes may or may not be situated on said second line.

At least one of the two upper holes is preferably configured to allow a plurality of implantation directions of the screw that the hole is intended to receive, and preferably both upper holes are configured to allow that plurality of implantation directions.

Thus, the screws placed in the upper holes can have different implantation directions relative to each other, thereby ensuring perfect anchoring of the plate and said extension to the fifth lumbar vertebra. In particular the screw of the lower hole can be oriented toward the bone of the lower vertebral plateau, while the screw of the upper hole can be oriented toward the bone of the upper vertebral plateau.

To the same end, at least one of the two lower holes, i.e. those intended to receive implantation screws in the sacrum, can be configured to allow a plurality of implantation directions of the screw that that hole is intended to receive, and preferably the two lower holes are configured to allow that plurality of implantation directions.

This or these holes may be in a hollow sphere portion and are capable to receive screws with sphere portion-shaped heads. Preferably, however, at least one of these holes is a hollow sphere portion and receives therein a circular ring with a peripheral face in the shape of a sphere portion, able to be engaged and retained in the hole with the possibility of multidirectional orientations relative to the plate, and the screw intended to be engaged in said ring comprises a spherical or sphere segment-shaped retaining portion containing the equator of said sphere, the diameter of which is such that said retaining portion can be placed in an adjusted manner in the housing defined by the ring.

According to one preferred embodiment of the invention, in that case, the outer peripheral face of the ring is in the shape of a segment of a first sphere and contains the equator of said first sphere, and the inner peripheral face of the ring is in the shape of a segment of a second sphere and contains the equator of said second sphere; the equator of the second sphere is offset relative to the equator of the first sphere along the axis of the ring, on the side of a first axial end of the ring, which is that by which the screw is intended to be inserted through the ring; the inner peripheral face of the ring defines, between the equator of said second sphere and said first end, jointly with said outer peripheral face, a proximal portion of the ring forming a first collar whereof the dimensions are such that said first collar can be elastically deformed by said retaining portion comprised by the screw, when the screw is inserted into said ring; the inner peripheral face of the ring defines, between the equator of said second sphere and the second axial end of the ring, opposite said first end, jointly with the outer peripheral face, a distal portion of the ring forming a second collar whereof the dimensions are such that said second collar cannot be elastically deformed by said retaining portion.

Preferably, the plate assumes a curved shape, the concavity of which is on the posterior surface of the plate, i.e. on the surface intended to come into contact with the vertebrae, and the convexity of which is on the anterior surface of the plate; and said extension is connected to the plate by an inflexion and protrudes therefrom while forming, on the anterior side of the plate, an obtuse angle with the zone of the plate to which it is connected, said angle being in the vicinity of 155°.

This specific shape is adapted to perfect bearing of the plate and the extension against the two bone parts to be immobilized.

Preferably, the plate comprises at least one lower tip protruding from its lower portion, intended to be inserted into the first vertebra of the sacrum, and preferably two sharp projections.

This or these sharp projections allow the plate to be prepositioned when said plate is being inserted, and thereby ensure complementary immobilization of the plate relative to the sacrum.

Advantageously, the plate comprises a means for assembly to an intervertebral implant intended to be inserted into the space comprised between the first vertebra of the sacrum and the fifth lumbar vertebra.

This intervertebral implant is intended to suitably reposition the fifth lumbar vertebra relative to the first vertebra of the sacrum. It can in particular be hollow and contain a bone graft making it possible to perform a bone solidification between the two vertebrae, by growth of the bone cells through said graft, which is commonly called a "vertebral fusion."

The invention will be better understood, and other features and advantages thereof will appear, in reference to the appended diagrammatic drawing, showing, as a non-limiting example, several embodiments of the osteosynthesis plate to which it relates.

DESCRIPTION OF THE PREFERRED EMBODIMENTS

For simplification, the elements that appear identically or similarly from one embodiment to the next will be designated using the same numerical references and will not be described again.

Figure 7:
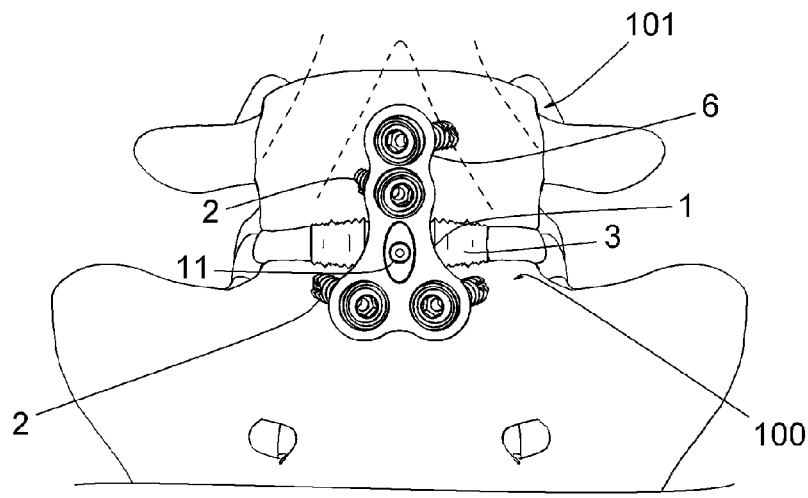
FIG. 7 is an anterior view of the sacrum and the fifth lumbar vertebra, after placement of the plate and an intervertebral implant, the bones being considered transparent for the clarity of the drawing.

FIGS. 1 to 4 show a plate 1 for the osteosynthesis of the lumbosacral joint. As appears in FIGS. 7 to 9, this plate 1 is intended to be placed on the first vertebra 100 of the sacrum and the fifth lumbar vertebra 101 and to be fixed to said vertebrae using screws 2. It can in particular be connected to an intervertebral implant 3 inserted between the plates of said vertebrae 100, 101, as shown by FIG. 7.

In reference to FIGS. 1 to 4, the plate 1 assumes a generally triangular shape, with rounded corners and concave edges, and comprises an upper extension 6. It will be understood that the terms "lower" and "upper" must be considered in relation to what is located in the lower position or upper position of the plate after implantation on a patient.

The plate 1 is intended to come opposite the vertebra 100 and the lower portion of the body of the vertebra 101; it comprises two juxtaposed lower holes 7, intended to receive implantation screws 2 in the sacrum, and a first upper hole 8 for receiving an implantation screw 2 in said body of the vertebra 101.

The plate 1 also comprises a central hole 9 emerging in the bottom of an oval counterbore 10. This hole 9 and counterbore 10 allow the plate 1 to be mounted on the end of a gripping and impaction instrument (the principle of which is well known and therefore not shown). The hole 9 can also be used to connect the plate 1 to said intervertebral implant 3, using a screw 11, as shown in FIG. 7.

The upper extension 6 is integral with the plate 1 and extends the upper end thereof, i.e. protrudes from the side opposite the two holes 7. It is intended to come opposite the middle height-wise, or even the upper portion of the body of the vertebra 101. It comprises a second upper hole 15 formed entirely thereon, for receiving a second implantation screw 2 in said body of the vertebra 101. As appears clearly in FIG. 4, the extension 6 has, at all points of its length, a width not more than twice the diameter of said second upper hole 15.

Figure 10:
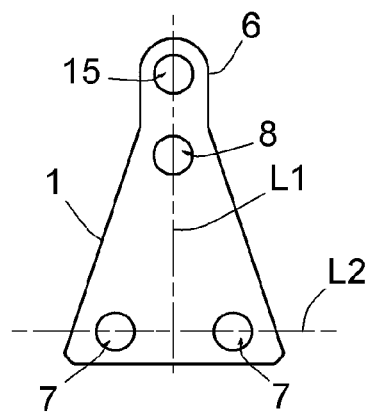
FIG. 10 is a diagrammatic view of the plate according to the first embodiment.

In reference to FIG. 10, which is a diagrammatic illustration of the plate 1 and the extension 6, it appears that the direction in which the extension 6 protrudes from the plate 1 is such that the first upper hole 8 and the second upper hole 15 are placed on a first line L1 substantially perpendicular to a second line L2 passing through the two juxtaposed lower holes 7.

Figure 1:
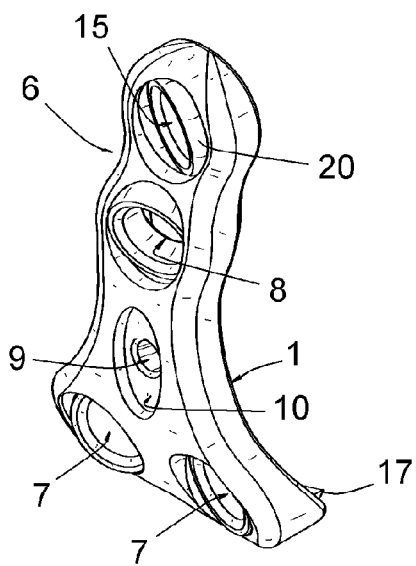
FIG. 1 is a perspective view according to a first embodiment.
Figure 2:
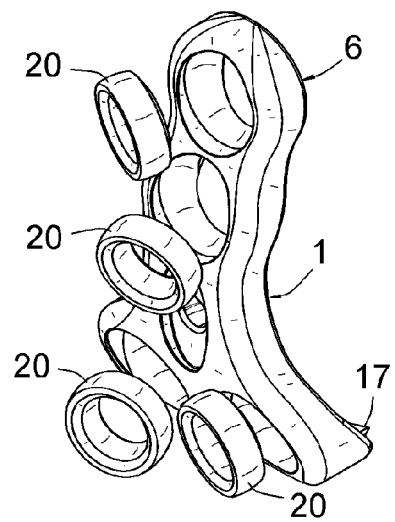
FIG. 2 is a view similar to FIG. 1, of the screw receiving rings it comprises, having been removed from their receiving holes.
Figure 3:
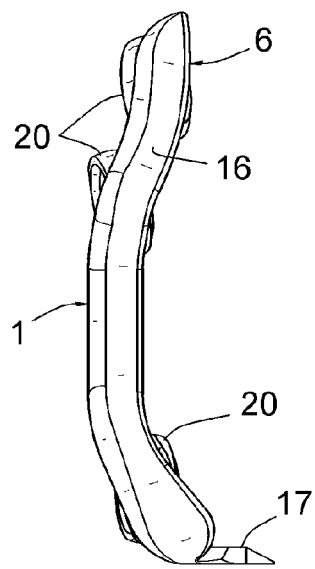
FIG. 3 is a side view.

FIG. 3 shows that the plate 1 has a curved shape, the concavity of which is located on the posterior face of the plate, i.e. on the face intended to come into contact with the vertebrae 100, 101; the convexity of said plate 1 is consequently located on the anterior face of said plate. The extension 6 is connected to the plate 1 by an inflexion 16 and extends while forming, on the anterior side of the plate 1, an obtuse angle with the portion of the plate 1 to which it is connected, in the vicinity of 155°.

It also appears in said FIG. 3 that the plate 1 has two lower sharp projections 17 protruding from its lower edge, in the anteroposterior direction of the plate 1. In reference in particular to FIG. 8, it appears that these sharp projections 17 are intended to be inserted into the first vertebra 100 of the sacrum.

Returning to FIG. 2, it appears that each hole 7, 8 and 15 is defined by a wall in the shape of a hollow sphere portion and that it receives a circular ring 20 therein with a sphere portion-shaped peripheral face. Said ring 20 is made from a material that is slightly elastically deformable, in particular PEEK (polyetheretherketone), and can be engaged and retained in the corresponding hole 7, 8, 15 by snapping, with the possibility of sliding relative to the plate 1 and the extension 6, and therefore multidirectional orientations relative to said plate 1 and said extension 6.

Figure 4:
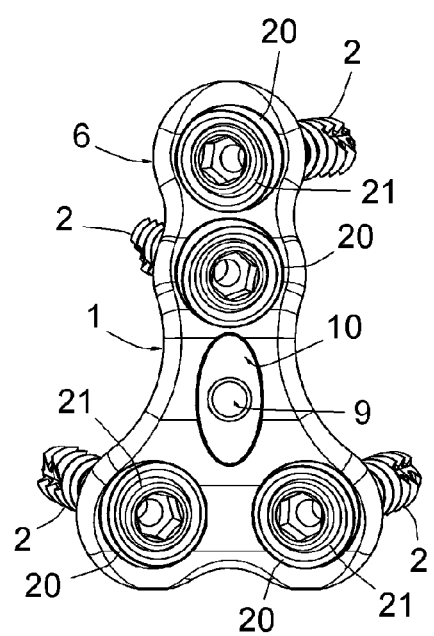
FIG. 4 is a front view of the screws ensuring its anchoring to the vertebrae being put in place.

In reference to FIG. 4, it is understood that each screw 2 has a spherical head 21, the diameter of which is such that said head 21 can be placed in an adjusted manner in the housing defined by a corresponding ring 20.

Figure 5:
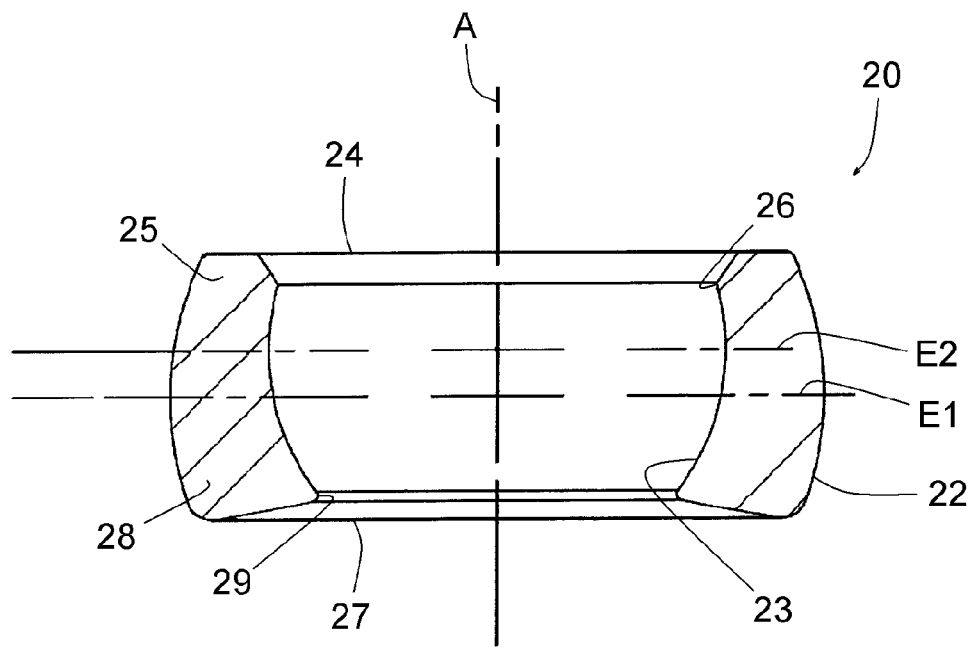
FIG. 5 is an enlarged cross-sectional view of a screw receiving ring.
Figure 6:
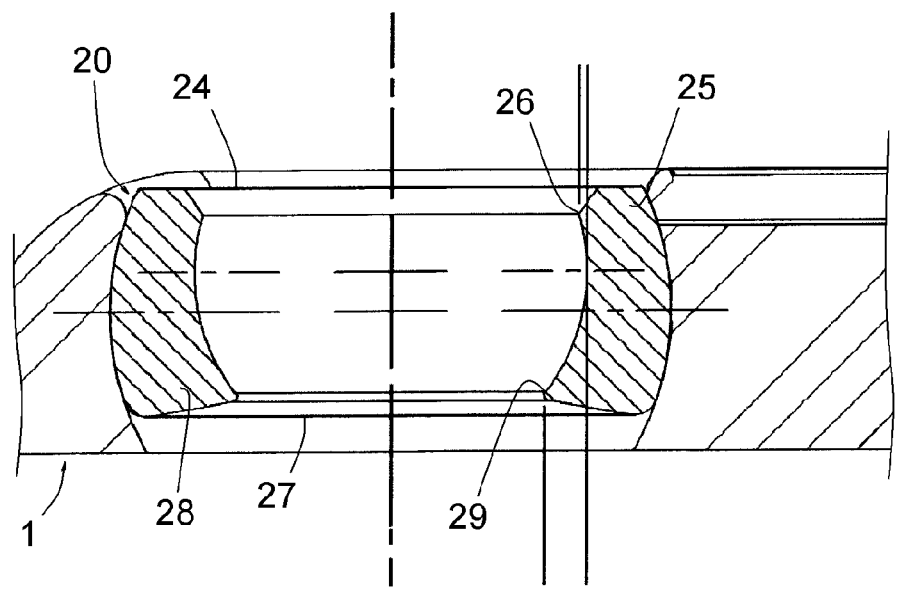
FIG. 6 is a view similar to FIG. 5, the ring being in place on the plate.

FIGS. 5 and 6 show a ring 20 in cross-section passing through its axis A. In reference to said figures, it appears that the outer peripheral surface 22 of the ring 20 is in the form of a segment of a first sphere containing the equator E1 of said first sphere, and that the inner peripheral surface 23 of the ring 20 is in the shape of a segment of a second sphere containing the equator E2 of said second sphere. The equator E2 of the second sphere is offset relative to the equator E1 of the first sphere along the axis A of the ring 20, on the side of a first axial end 24 of the ring, which is that by which the screw 2 is intended to be inserted through the ring 20; the inner peripheral surface 23 defines, between the equator E2 of said second sphere and said first end, jointly with said outer peripheral surface 22, a proximal portion 25 of the ring 20 forming a first collar 26 whereof the dimensions are such that said first collar 26 can be elastically deformed by the head 21 of the screw 2, during the insertion of the screw 2 into said ring 20. The inner peripheral surface 23 of the ring 20 defines, between the equator E2 of said second sphere and the second axial end 27 of the ring 20, opposite said first end 24, jointly with the outer peripheral surface 22, a distal portion 28 of the ring 20 forming a second collar 29 whereof the dimensions are such that said second collar 29 cannot be elastically deformed by the head 21 of the screw 2.

FIG. 6 shows that the diameter of the ring 20 is such that said outer peripheral wall 22 comes into the immediate vicinity of the wall of the plate 1 defining the hole 7, 8 or 15 receiving the ring 20. The ring 20 can, however, slide along said wall, so that it can be placed in a plurality of directional orientations, as appears in particular in FIGS. 1 and 3.

In practice, after preparing the intervertebral space to receive the implant 3, the plate 1, with the implant 3 connected to it, is impacted on the vertebrae 100 and 101 so as to insert the sharp projections 17 into the vertebra 100. The two holes 7 are then opposite said vertebra 100 while the holes 8 and 15 are respectively opposite the lower portion and the middle portion of the vertebral body of the vertebra 101.

Figure 8:
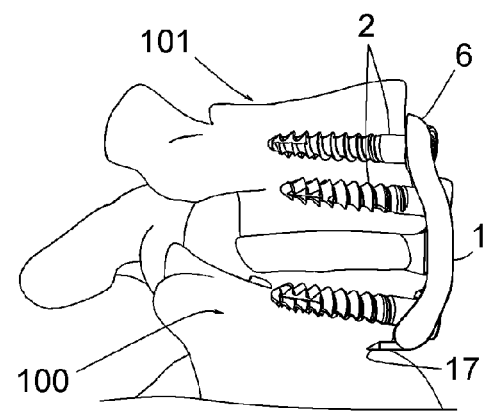
FIG. 8 is a sagittal view.
Figure 9:
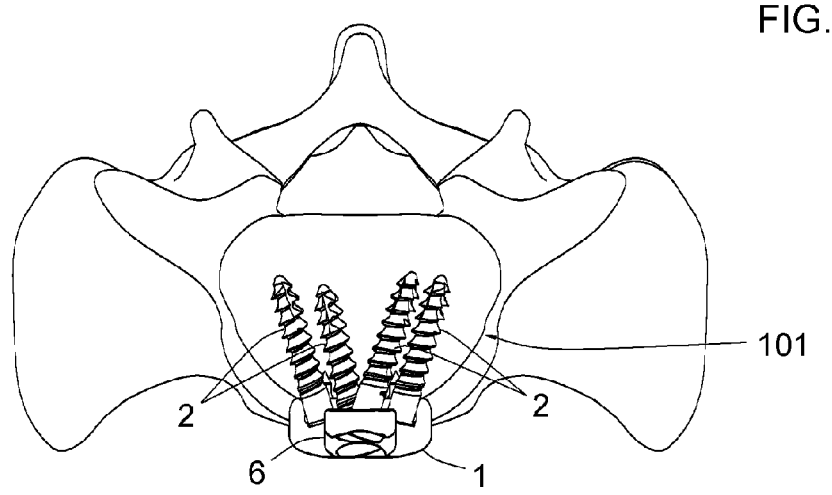
FIG. 9 is a cervico-caudal view.

Due to its triangular shape, the plate 1 is adapted to be placed in the lower portion of the space defined by the lower branches of the bifurcations of the vena cave (iliac veins) and the aorta (iliac arteries), opposite the first vertebra 100 of the sacrum; the extension 6 is adapted to be placed in the upper portion of said same space, opposite the fifth lumbar vertebra 101. The reduced width of the extension 6 makes it possible to reduce the work to mobilize the bifurcations of the vena cave and the aorta, or even to eliminate that work. Furthermore, the aforementioned specific shape of the profile of the plate 1 and the extension 6 allows the assembly to be adapted to perfect bearing against the bodies of the vertebrae 100, 101, as shown in FIG. 8.

The rings 20 are then oriented so as to give the respective pairs of screws 2 directions diverging in horizontal planes or, particularly concerning the two upper screws, in a vertical and/or horizontal plane. These divergences make it possible to ensure complete anchoring of the plate 1-extension 6 assembly in several directions and allow the screws 2 to bear with resistance in the hard cortical bone. In particular, the two upper screws 2, when they are divergent in a vertical plane, can thus bear in the cortical walls forming the upper and lower plates of the fifth lumbar vertebra 101.

At the end of screwing, the heads 21 of the screws 2 forcibly cross said first collars 26 of the rings 20, which ensures their axial retention in the rings 20, and thus prevents the risk of them backing out by unscrewing under the effect of the repeated stresses that such a plate is made to undergo. These heads 21 cannot, however, cross the collars 29 of said same rings 20.

Figure 11:
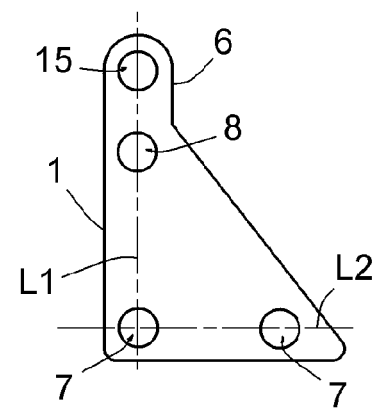
FIG. 11 is a diagrammatic view of the plate according to a second embodiment.
Figure 12:
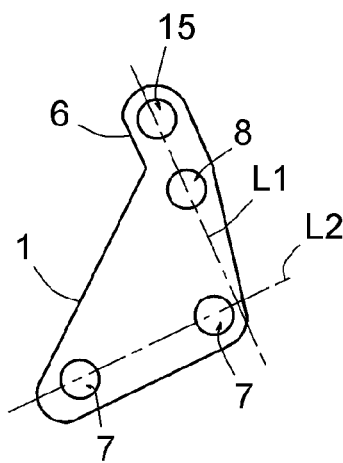
FIG. 12 is a diagrammatic view of the plate according to a third embodiment.

FIGS. 11 and 12 show that the plate 1 can have different shapes, for example a right-angled triangle shape in the case of the plate shown in FIG. 11 or a shape with any triangle in the case of the plate shown in FIG. 12. In any case, the hole 8 and the hole 15 are placed on said first line L1, which is substantially perpendicular to said second line L2 passing through the two juxtaposed lower holes 7.

As appears from the preceding, the invention provides a plate for the osteosynthesis of the lumbosacral joint having the decisive advantage of allowing both perfect fixing in the fifth lumbar vertebra and reduced or nonexistent mobilization of the bifurcations of the vena cave and the aorta.

The invention was described above in reference to an embodiment provided as an example. It is of course not limited to that embodiment, but extends to all other embodiments covered by the appended claims.

What is claimed is:

1. A plate for the osteosynthesis of the lumbosacral joint comprising:

the plate having a contour having a curved triangular shape defining a small end and an opposite large end, the plate including an upper side located on the small end of the triangle, a middle section, lateral sides, a front side, a posterior side, a lower side located on the large end of the triangle, and a concavity facing the posterior side of the plate;

two juxtaposed lower holes located on the lower side of the plate, each one of the lower holes includes a center, the centers of the lower holes are separated by a first distance;

a counterbore located on the middle section of the plate, the counterbore is located above and between the lower holes;

a central hole located on the counterbore;

a first upper hole located on the upper side of the plate and above the counterbore;

an extension integral with the plate, the extension having a width smaller than a width of the upper side of the plate and a length that continuously projects and passes the upper side of the plate longitudinally extending the length of the plate upper side the extension forms an inflexion at the upper end of the plate forming an angle that faces the posterior side of the plate;

a second upper hole formed in the extension, the second upper hole is formed on the entire length of the extension;

a first fastener to be inserted into each one of the lower holes;

a second fastener to be inserted into the first upper hole; and a third fastener to be inserted into the second upper hole.

2. The plate according to claim 1, wherein the first and second upper holes include a wall having the shape of a hollow sphere.

3. The plate according to claim 1, wherein:
the inflexion is an obtuse angle with a zone of the plate to which it is connected, said angle being approximately 155°.

4. The plate according to claim 1, further comprising at least one sharp projection protruding from lower end of the plate.

5. A plate for the osteosynthesis of the lumbosacral joint comprising:

the plate having a contour having a curved triangular shape defining a small end and an opposite large end, the plate includes an upper side located on the small end of the triangle, a middle section, lateral sides, a front side, a posterior side, a lower side located on the large end of the triangle, and a concavity facing the posterior side of the plate;

two juxtaposed lower holes located on the lower side of the plate, each lower hole includes a center, the centers of the lower holes are separated by a first distance the two juxtaposed lower holes have each a same, identical, first diameter;

a counterbore located on the middle section of the plate, the counterbore is located above and between the lower holes;

a central hole located on the counterbore;

a first upper hole located on the upper side of the plate and above the counterbore; the first upper hole is adapted to receive an implantation screw in the fifth lumbar vertebra, the first upper hole has a second diameter, the second diameter is identical to the first diameter;

an extension integral with the plate, the extension having a width smaller than a width of the upper side of the plate and a length that continuously projects and passes the upper side of the plate longitudinally extending the length of the plate upper side, the extension forms an inflexion at the upper end of the plate forming an angle that faces the posterior side of the plate;

a second upper hole formed in the extension, the second upper hole is formed on the entire length of the extension;

at least one sharp projection integral with the plate and protruding from the lower end of the plate and towards the posterior side of the plate;

a ring placed inside at least one of the first upper hole, the second upper hole, or the lower holes, the ring is made of an elastically deformable material;

a first fastener to be inserted into each one of the lower holes;

a second fastener to be inserted into the first upper hole; and a third fastener to be inserted into the second upper hole.

6. A plate for the osteosynthesis of the lumbosacral joint comprising:

the plate having a contour having a curved triangular shape defining a small end and an opposite large end, the plate includes an upper side located on the small end of the triangle, a middle section, lateral sides, a front side, a posterior side, a lower side located on the large end of the triangle, and a concavity facing the posterior side of the plate;

two juxtaposed lower holes located on the lower side of the plate, each lower hole includes a center, the centers of the lower holes are separated by a first distance the two juxtaposed lower holes have each a same, identical, first diameter;

an oval counterbore located on the middle section of the plate, the oval counterbore is located above and between the lower holes;

a central hole located on the oval counterbore;

a first upper hole located on the upper side of the plate and above the counterbore; the first upper hole is adapted to receive a first implantation screw in the fifth lumbar vertebra, the first upper hole has a second diameter, the second diameter is identical to the first diameter;

an extension integral with the plate, the extension having a width smaller than a width of the upper side of the plate and a length that continuously projects and passes the upper side of the plate longitudinally extending the length of the plate, upper side the extension forms an inflexion at the upper end of the plate forming an angle that faces the posterior side of the plate;

a second upper hole formed in the extension, the second upper hole is formed on the entire length of the extension; the second upper hole is adapted to receive a second implantation screw in the fifth lumbar vertebra, the second upper hole has a third diameter, the third diameter is identical to the second diameter;

a ring placed inside at least one of the first upper hole, the second upper hole, or the lower holes, the ring is made of an elastically deformable material;

a first fastener to be inserted into each one of the lower holes;

a second fastener to be inserted into the first upper hole; and a third fastener to be inserted into the second upper hole.

7. The plate according to claim 1, wherein the plate is hollow and contains a bone graft.

8. The plate according to claim 6, wherein each ring has an outer surface having a first center and an inner surface having a second center, the first center is offset relative to the second center.

* * * * *